US009514276B2

(12) United States Patent
Daynes et al.

(10) Patent No.: US 9,514,276 B2
(45) Date of Patent: Dec. 6, 2016

(54) MANUALLY INITIATING WIRELESS TRANSMISSION OF RESUSCITATION EVENT DATA TO MEDICAL DEVICE

(75) Inventors: Nathan Woodruff Daynes, Snoqualmie, WA (US); John Carlton Daynes, Redmond, WA (US)

(73) Assignee: PHYSIO-CONTROL, INC., Redmond, WA (US)

( * ) Notice: Subject to any disclaimer, the term of this patent is extended or adjusted under 35 U.S.C. 154(b) by 784 days.

(21) Appl. No.: 13/191,334

(22) Filed: Jul. 26, 2011

(65) Prior Publication Data

US 2012/0123490 A1 May 17, 2012

Related U.S. Application Data

(60) Provisional application No. 61/413,297, filed on Nov. 12, 2010.

(51) Int. Cl.
*G06F 19/00* (2011.01)
*A61N 1/39* (2006.01)

(52) U.S. Cl.
CPC ......... *G06F 19/3406* (2013.01); *A61N 1/3925* (2013.01); *A61N 1/39* (2013.01); *G06F 19/322* (2013.01); *G06F 19/3481* (2013.01)

(58) Field of Classification Search
CPC G06F 19/3406; G06F 19/322; G06F 19/3481; A61N 1/3925; A61N 1/39
USPC .................. 607/2, 4–5, 59–60; 128/903–904
See application file for complete search history.

(56) References Cited

U.S. PATENT DOCUMENTS

| 5,697,954 | A | * | 12/1997 | Sears et al. | 607/5 |
| 5,999,851 | A | * | 12/1999 | White | 607/5 |
| 6,141,584 | A | | 10/2000 | Rockwell et al. | |
| 6,377,892 | B1 | * | 4/2002 | Johnson et al. | 701/470 |
| 8,315,711 | B2 | * | 11/2012 | Campos et al. | 607/72 |
| 2007/0233199 | A1 | * | 10/2007 | Moore et al. | 607/6 |
| 2009/0030334 | A1 | * | 1/2009 | Anderson et al. | 600/528 |
| 2011/0314168 | A1 | * | 12/2011 | Bathiche et al. | 709/228 |

FOREIGN PATENT DOCUMENTS

| WO | 2004061704 A2 | 7/2004 |
| WO | 2007034394 A2 | 3/2007 |

OTHER PUBLICATIONS

International Search Report and Written Opinion, Patent Cooperation Treaty, Apr. 5, 2012, 13 pages, PCT/US2011/058664, European Patent Office.
Sascha Seagan, Review: Bump, the 1 Billionth iPhone App, Mar. 24, 2009, XP002672033, Retrieved from the Internet: URL: http://www.pcmag.com/article2/0,2817,2345899,00.asp, retrieved on Mar. 21, 2012.

(Continued)

*Primary Examiner* — Catherine Voorhees
(74) *Attorney, Agent, or Firm* — Marger Johnson

(57) ABSTRACT

An external defibrillator can include a bump sensor for generating motion information and a bump detector for determining whether the external defibrillator has been subjected to a local bump event. The external defibrillator can transmit wirelessly a data signal encoding resuscitation event data to a second external defibrillator over a wireless communication link between the two devices.

33 Claims, 10 Drawing Sheets

DEFIBRILLATION SCENE

BUMPING

(56) References Cited

OTHER PUBLICATIONS

Matt Hamblen: Bump app draws buzz at CTIA, Sep. 8, 2009, XP002672034, Retrieved from the Internet: URL: http://www.computerworld.com/s/article/9139163/Bump_app_draws_buzz_at_CTIA, retrieved on Mar. 21, 2012.

Eric Benderoff, New iPhone app works by bump, not touch, Mar. 30, 2009, XP002672036, Retrieved from the Internet: URL: http://featuresblogs.chicagotribune.com/eric2_0/2009/03/new-iphone-app-works-by-bump-not-touch.html, retrieved on Mar. 21, 2012.

* cited by examiner

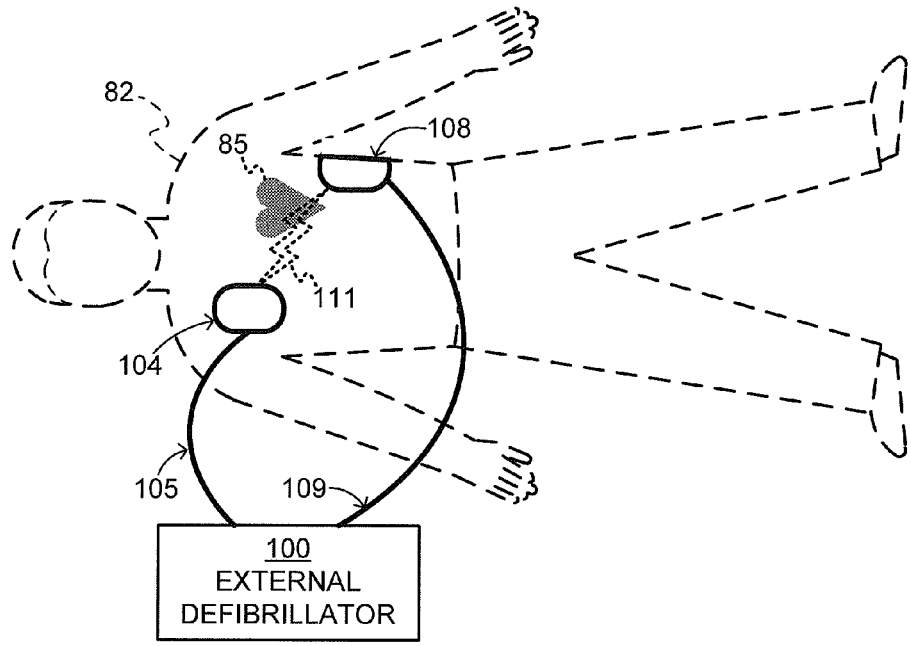
FIG. 1  *DEFIBRILLATION SCENE*
| TYPE OF EXTERNAL DEFIBRILLATOR | INTENDED TO BE USED BY PERSONS: | |
|---|---|---|
|  | IN THE MEDICAL PROFESSIONS | NOT IN THE MEDICAL PROFESSIONS |
| DEFIBRILLATOR – MONITOR | √ |  |
| AED | √ | √ |
FIG. 2  *TWO MAIN TYPES OF EXTERNAL DEFIBRILLATORS*

COMPONENTS OF EXTERNAL DEFIBRILLATOR

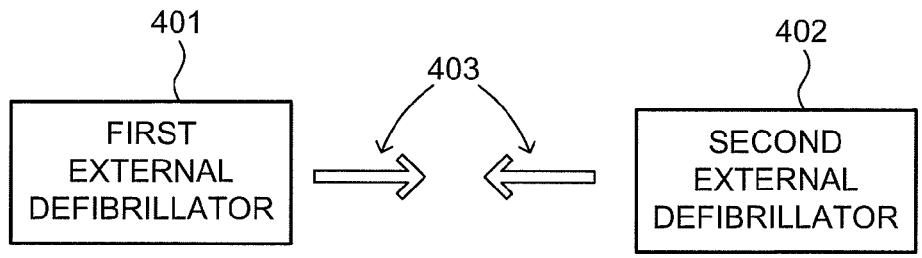
FIG. 4A   *BEFORE BUMPING*
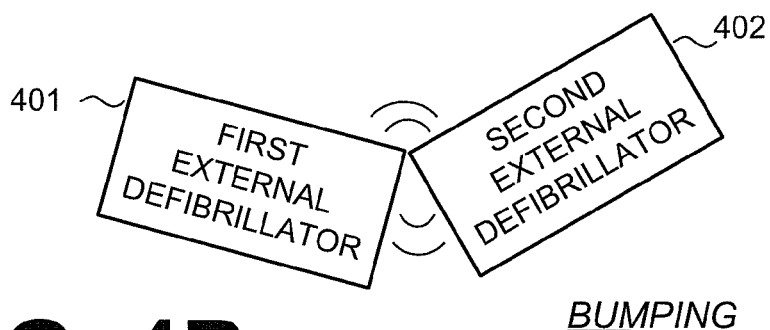
FIG. 4B   *BUMPING*
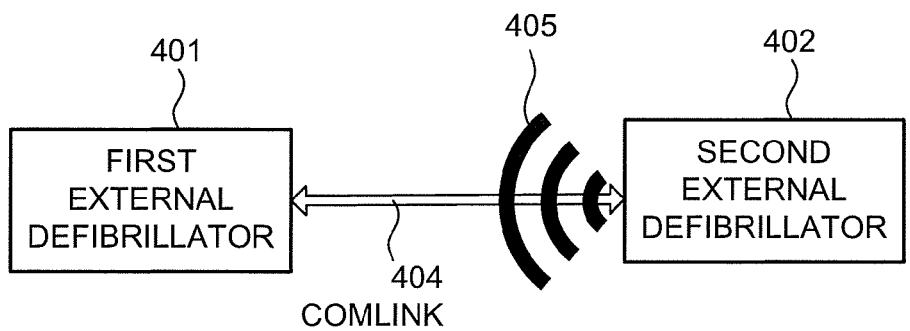
FIG. 4C   *AFTER BUMPING: EVENT DATA TRANSFER*

*EXTERNAL DEFIBRILLATOR
INITIATING RECEPTION OF EVENT
DATA UPON BEING BUMPED*

*METHODS OF EXTERNAL DEFIBRILLATOR RECEIVING EVENT DATA UPON BEING BUMPED*

FIG. 7 — METHODS OF ESTABLISHING COMMUNICATION LINK BETWEEN EXTERNAL DEFIBRILLATORS

EXTERNAL DEFIBRILLATOR
INITIATING TRANSMISSION OF EVENT
DATA UPON BEING BUMPED

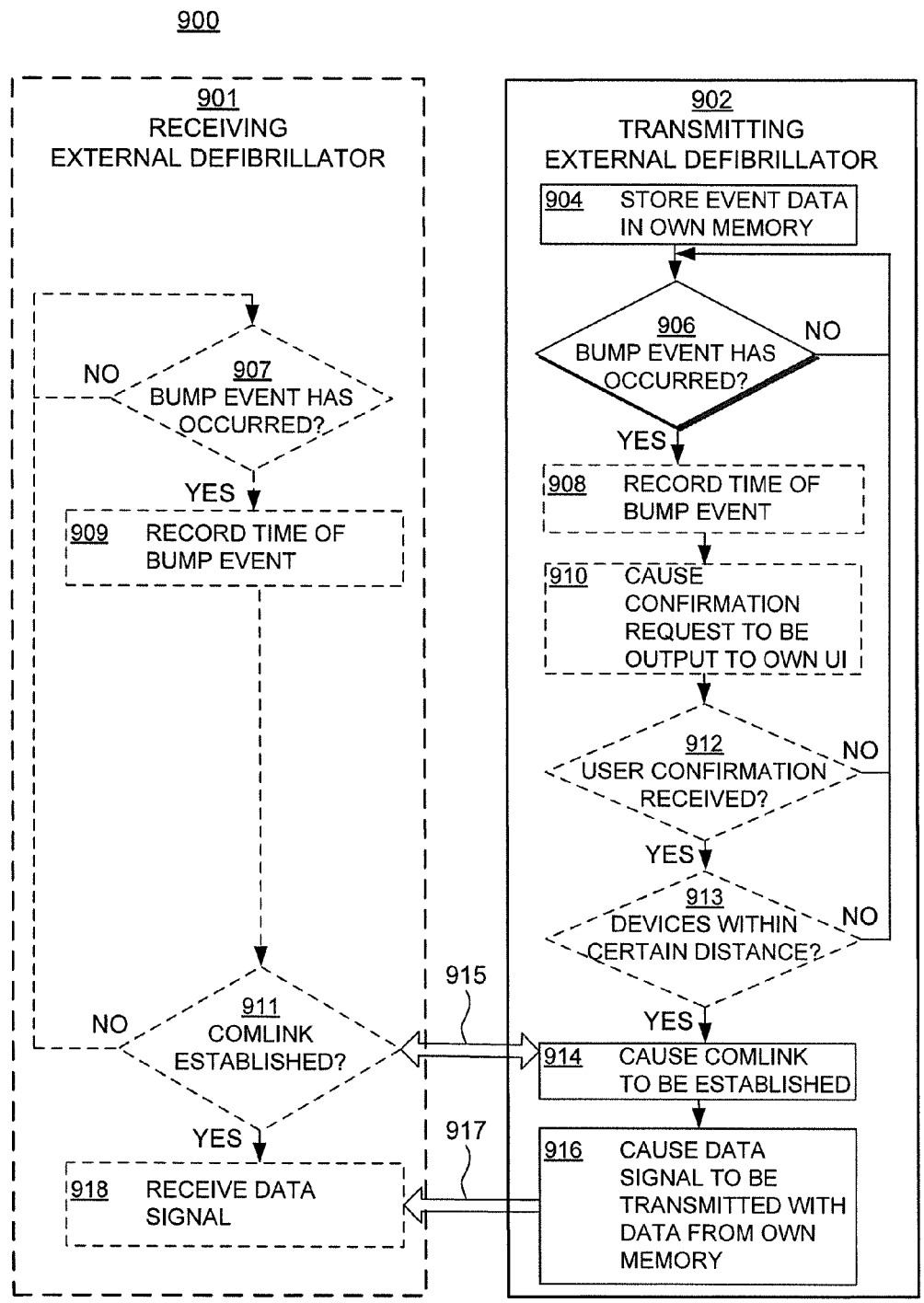
FIG. 9 — METHODS OF EXTERNAL DEFIBRILLATOR TRANSMITTING EVENT DATA UPON BEING BUMPED

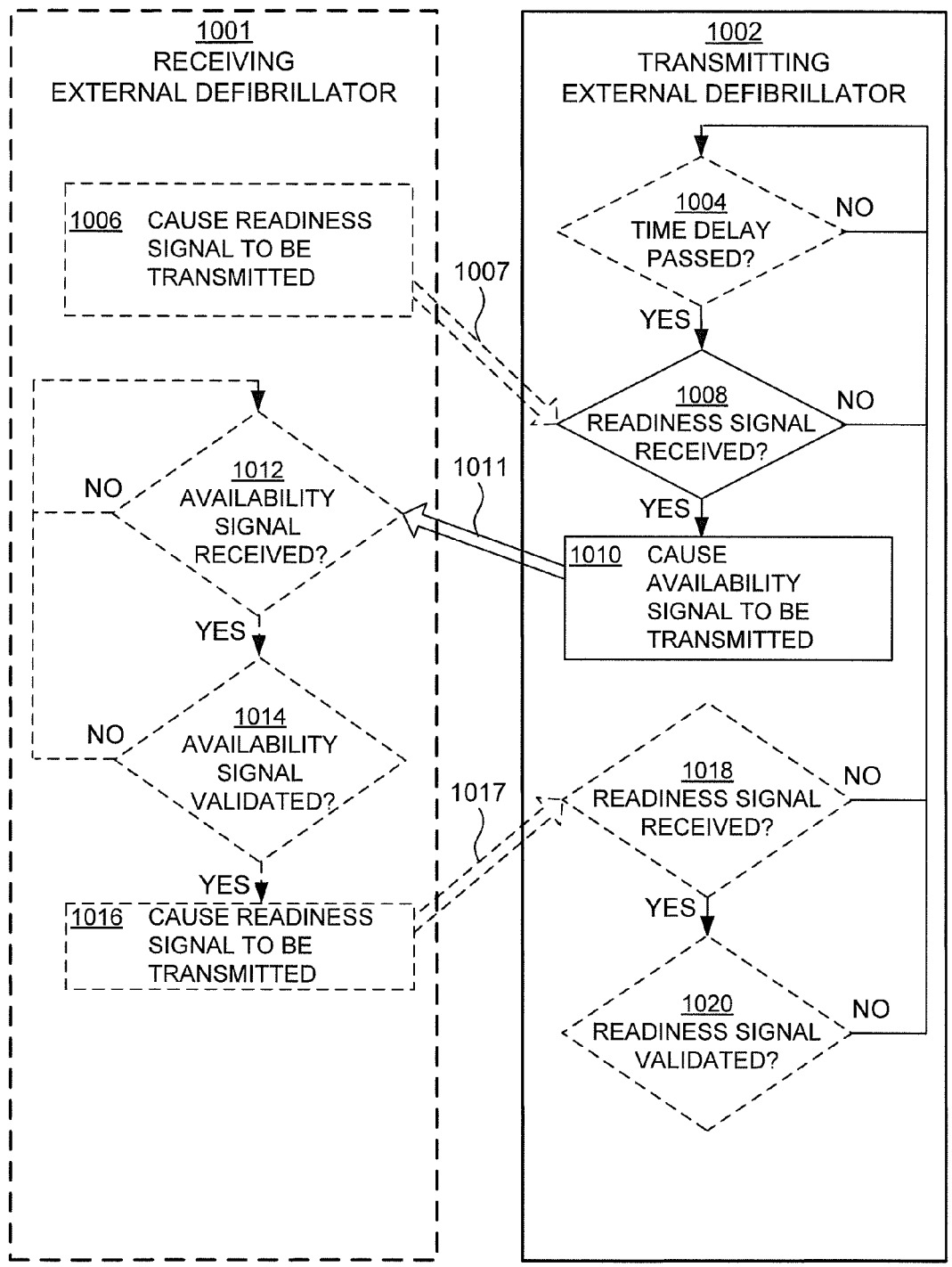
FIG. 10 — METHODS OF ESTABLISHING COMMUNICATION LINK BETWEEN EXTERNAL DEFIBRILLATORS

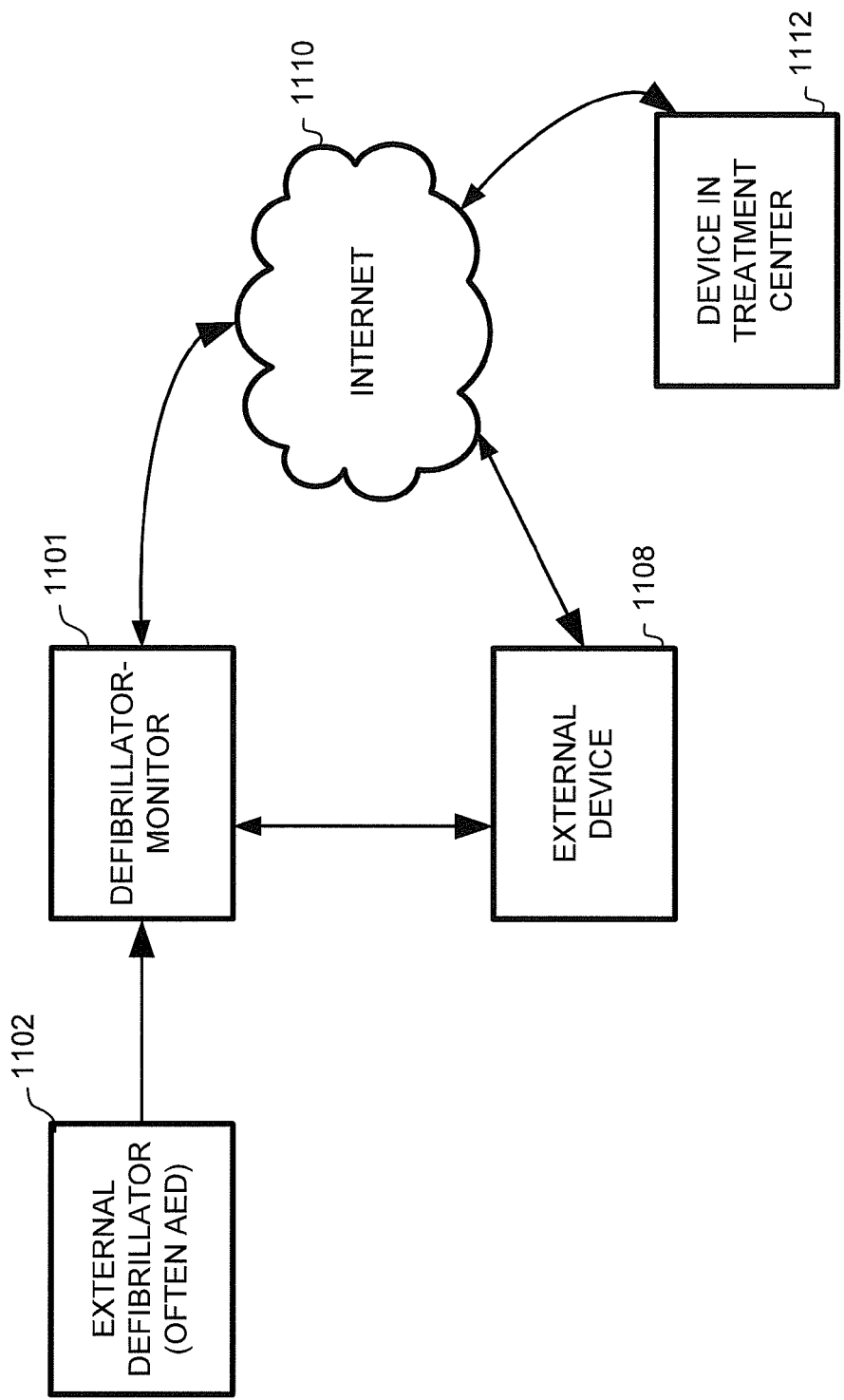

MANUALLY INITIATING WIRELESS TRANSMISSION OF RESUSCITATION EVENT DATA TO MEDICAL DEVICE

RELATIONSHIP WITH OTHER APPLICATIONS

This patent application claims priority from U.S.A. Provisional Patent Application Ser. No. 61/413,297, filed on Nov. 12, 2010, the disclosure of which is hereby incorporated by reference for all purposes.

This patent application may be found to be related to U.S.A. patent application Ser. No. 13/191,320, entitled MANUALLY INITIATING WIRELESS RECEPTION OF RESUSCITATION EVENT DATA FROM MEDICAL DEVICE, assigned to the same assignee, filed on the same day as the instant patent application.

FIELD

This invention generally relates to the field of medical devices such as defibrillators.

BACKGROUND

In humans, the heart beats to sustain life. In normal operation, it pumps blood through the various parts of the body. More particularly, the various chamber of the heart contract and expand in a periodic and coordinated fashion, which causes the blood to be pumped regularly. More specifically, the right atrium sends deoxygenated blood into the right ventricle. The right ventricle pumps the blood to the lungs, where it becomes oxygenated, and from where it returns to the left atrium. The left atrium pumps the oxygenated blood to the left ventricle. The left ventricle, then, expels the blood, forcing it to circulate to the various parts of the body.

The heart chambers pump because of the heart's electrical control system. More particularly, the sinoatrial (SA) node generates an electrical impulse, which generates further electrical signals. These further signals cause the above-described contractions of the various chambers in the heart, in the correct sequence. The electrical pattern created by the sinoatrial (SA) node is called a sinus rhythm.

Sometimes, however, the electrical control system of the heart malfunctions, which can cause the heart to beat irregularly, or not at all. The cardiac rhythm is then generally called an arrhythmia. Arrhythmias may be caused by electrical activity from locations in the heart other than the SA node. Some types of arrhythmia may result in inadequate blood flow, thus reducing the amount of blood pumped to the various parts of the body. Some arrhythmias may even result in a Sudden Cardiac Arrest (SCA). In a SCA, the heart fails to pump blood effectively, and, if not treated, death can occur. In fact, it is estimated that SCA results in more than 250,000 deaths per year in the United States alone. Further, a SCA may result from a condition other than an arrhythmia.

One type of arrhythmia associated with SCA is known as Ventricular Fibrillation (VF). VF is a type of malfunction where the ventricles make rapid, uncoordinated movements, instead of the normal contractions. When that happens, the heart does not pump enough blood to deliver enough oxygen to the vital organs. The person's condition will deteriorate rapidly and, if not reversed in time, they will die soon, e.g. within ten minutes.

Ventricular Fibrillation can often be reversed using a life-saving device called a defibrillator. A defibrillator, if applied properly, can administer an electrical shock to the heart. The shock may terminate the VF, thus giving the heart the opportunity to resume pumping blood. If VF is not terminated, the shock may be repeated, often at escalating energies.

A challenge with defibrillation is that the electrical shock must be administered very soon after the onset of VF. There is not much time: the survival rate of persons suffering from VF decreases by about 10% for each minute the administration of a defibrillation shock is delayed. After about 10 minutes the rate of survival for SCA victims averages less than 2%.

The challenge of defibrillating early after the onset of VF is being met in a number of ways. First, for some people who are considered to be at a higher risk of VF or other heart arrythmias, an Implantable Cardioverter Defibrillator (ICD) can be implanted surgically. An ICD can monitor the person's heart, and administer an electrical shock as needed. As such, an ICD reduces the need to have the higher-risk person be monitored constantly by medical personnel.

Regardless, VF can occur unpredictably, even to a person who is not considered at risk. As such, VF can be experienced by many people who lack the benefit of ICD therapy. When VF occurs to a person who does not have an ICD, they collapse, because blood flow has stopped. They should receive therapy quickly.

For a VF victim without an ICD, a different type of defibrillator can be used, which is called an external defibrillator. External defibrillators have been made portable, so they can be brought to a potential VF victim quickly enough to revive them.

During VF, the person's condition deteriorates, because the blood is not flowing to the brain, heart, lungs, and other organs. Blood flow must be restored, if resuscitation attempts are to be successful.

Cardiopulmonary Resuscitation (CPR) is one method of forcing blood flow in a person experiencing cardiac arrest. In addition, CPR is the primary recommended treatment for some patients with some kinds of non-VF cardiac arrest, such as asystole and pulseless electrical activity (PEA). CPR is a combination of techniques that include chest compressions to force blood circulation, and rescue breathing to force respiration.

Properly administered CPR provides oxygenated blood to critical organs of a person in cardiac arrest, thereby minimizing the deterioration that would otherwise occur. As such, CPR can be beneficial for persons experiencing VF, because it slows the deterioration that would otherwise occur while a defibrillator is being retrieved. Indeed, for patients with an extended down-time, survival rates are higher if CPR is administered prior to defibrillation.

Advanced medical devices can actually coach a rescuer who performs CPR. For example, a medical device can issue instructions, and even prompts, for the rescuer to perform CPR more effectively.

BRIEF SUMMARY

The present description gives instances of medical devices, software and methods, the use of which may help overcome problems and limitations of the prior art.

In some embodiments, a transmitting external defibrillator having a housing may transmit resuscitation event data to a receiving external defibrillator. For example, a bump sensor of the transmitting external defibrillator may generate motion information of the housing and a bump detector may determine whether the housing has been subjected to a local bump event based on the generated motion information.

Responsive to a determination that the local bump event has occurred, a processor of the transmitting external defibrillator may cause communication modules of the external defibrillators to establish a wireless communication link. Once the communication link has been established, the transmitting external defibrillator may wirelessly transmit the resuscitation event data to the receiving external defibrillator over the communication link.

An advantage over the prior art is that resuscitation event data may be transferred quickly, easily, and securely from a first external defibrillator to a second external defibrillator. Such data transfer may be performed independent of a user needing to physically establish a connection between the devices by plugging wires into either device, for example. Indeed, certain embodiments use only a local bump event to initiate a process that ultimately causes the data transfer to take place. As used herein, a bump event generally refers to a user causing one of the external defibrillators to physically bump the other external defibrillator.

These and other features and advantages of this description will become more readily apparent from the following Detailed Description, which proceeds with reference to the drawings, in which:

BRIEF DESCRIPTION OF THE DRAWINGS

FIG. 1 is a diagram of a scene where an external defibrillator is used to save the life of a person according to embodiments.

FIG. 2 is a table listing two main types of the external defibrillator shown in FIG. 1, and who they might be used by.

FIG. 4A is a diagram showing two external defibrillators before being bumped together according to embodiments.

FIG. 4B is a diagram showing the two external defibrillators of FIG. 4A being bumped together, according to embodiments.

FIG. 4C is a diagram showing the two external defibrillators of FIG. 4B establishing a communication link, after having been bumped together according to embodiments.

FIG. 9 is a flowchart for illustrating example methods executable by external defibrillators according to embodiments.

FIG. 10 is a flowchart for illustrating example methods executable by external defibrillators according to embodiments.

FIG. 11 is a block diagram showing systems for transferring event data that include an external defibrillator and a defibrillator-monitor according to embodiments.

DETAILED DESCRIPTION

Figure 3:
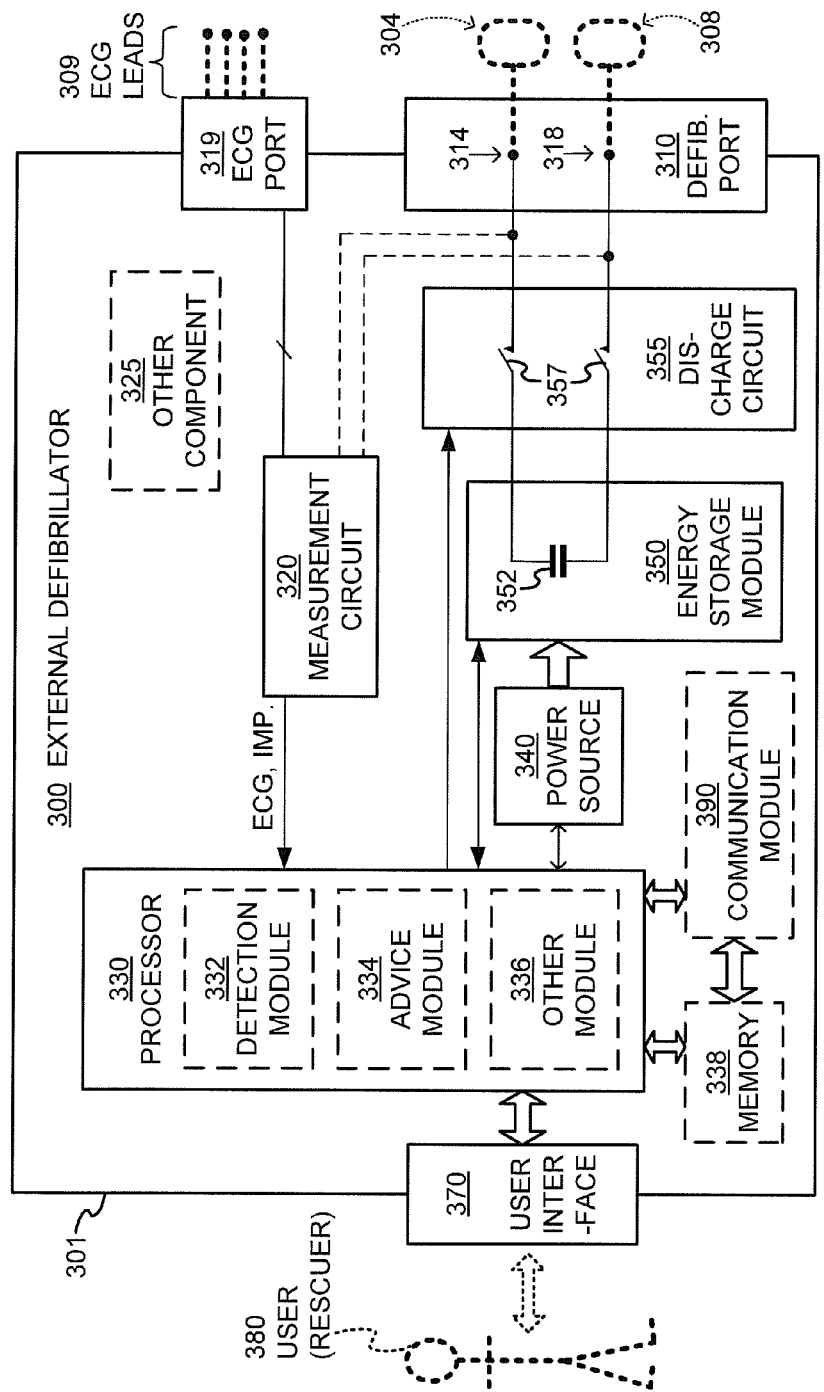
FIG. 3 is a functional block diagram showing components of an external defibrillator, such as the one shown in FIG. 1, which is made according to embodiments.

FIG. 1 is a diagram of a defibrillation scene. A person 82 is lying on their back. Person 82 could be a patient in a hospital, or someone found unconscious, and then turned to be on their back. Person 82 is experiencing a condition in their heart 85, which could be Ventricular Fibrillation (VF).

A portable external defibrillator 100 has been brought close to person 82. At least two defibrillation electrodes 104, 108 are usually provided with external defibrillator 100, and are sometimes called electrodes 104, 108. Electrodes 104, 108 are coupled with external defibrillator 100 via respective electrode leads 105, 109. A rescuer (not shown) has attached electrodes 104, 108 to the skin of person 82. Defibrillator 100 is administering, via electrodes 104, 108, a brief, strong electric pulse 111 through the body of person 82. Pulse 111, also known as a defibrillation shock, goes also through heart 85, in an attempt to restart it, for saving the life of person 82.

Defibrillator 100 can be one of different types, each with different sets of features and capabilities. The set of capabilities of defibrillator 100 is determined by planning who would use it, and what training they would be likely to have. Examples are now described.

FIG. 2 is a table listing two main types of external defibrillators, and who they are primarily intended to be used by. A first type of defibrillator 100 is generally called a defibrillator-monitor, because it is typically formed as a single unit in combination with a patient monitor. A defibrillator-monitor is sometimes called monitor-defibrillator. A defibrillator-monitor is intended to be used by persons in the medical professions, such as doctors, nurses, paramedics, emergency medical technicians, etc. Such a defibrillator-monitor is intended to be used in a pre-hospital or hospital scenario.

As a defibrillator, the device can be one of different varieties, or even versatile enough to be able to switch among different modes that individually correspond to the varieties. One variety is that of an automated defibrillator, which can determine whether a shock is needed and, if so, charge to a predetermined energy level and instruct the user to administer the shock. Another variety is that of a manual defibrillator, where the user determines the need and controls administering the shock.

As a patient monitor, the device has features additional to what is minimally needed for mere operation as a defibrillator. These features can be for monitoring physiological indicators of a person in an emergency scenario. These physiological indicators are typically monitored as signals. For example, these signals can include a person's full ECG (electrocardiogram) signals, or impedance between two electrodes. Additionally, these signals can be about the person's temperature, non-invasive blood pressure (NIBP), arterial oxygen saturation/pulse oximetry (SpO2), the concentration or partial pressure of carbon dioxide in the respiratory gases, which is also known as capnography, and so on. These signals can be further stored and/or transmitted as patient data.

A second type of external defibrillator 100 is generally called an AED, which stands for "Automated External Defibrillator". An AED typically makes the shock/no shock determination by itself, automatically. Indeed, it can sense enough physiological conditions of the person 82 via only the shown defibrillation electrodes 104, 108 of FIG. 1. In its present embodiments, an AED can either administer the shock automatically, or instruct the user to do so, e.g. by pushing a button. Being of a much simpler construction, an AED typically costs much less than a defibrillator-monitor. As such, it makes sense for a hospital, for example, to deploy AEDs at its various floors, in case the more expensive defibrillator-monitor is more critically being deployed at an Intensive Care Unit, and so on.

AEDs, however, can also be used by people who are not in the medical profession. More particularly, an AED can be used by many professional first responders, such as policemen, firemen, etc. Even a person with only first-aid training can use one. And AEDs increasingly can supply instructions to whoever is using them.

AEDs are thus particularly useful, because it is so critical to respond quickly, when a person suffers from VF. Indeed, the people who will first reach the VF sufferer may not be in the medical professions.

Increasing awareness has resulted in AEDs being deployed in public or semi-public spaces, so that even a member of the public can use one, if they have obtained first aid and CPR/AED training on their own initiative. This way, defibrillation can be administered soon enough after the onset of VF, to hopefully be effective in rescuing the person.

There are additional types of external defibrillators, which are not listed in FIG. 2. For example, a hybrid defibrillator can have aspects of an AED, and also of a defibrillator-monitor. A usual such aspect is additional ECG monitoring capability.

FIG. 3 is a diagram showing components of an external defibrillator 300 made according to embodiments. These components can be, for example, in external defibrillator 100 of FIG. 1. Plus, these components of FIG. 3 can be provided in a housing 301, which is also known as casing 301.

External defibrillator 300 is intended for use by a user 380, who would be the rescuer. Defibrillator 300 typically includes a defibrillation port 310, such as a socket in housing 301. Defibrillation port 310 includes nodes 314, 318. Defibrillation electrodes 304, 308, which can be similar to electrodes 104, 108, can be plugged in defibrillation port 310, so as to make electrical contact with nodes 314, 318, respectively. It is also possible that electrodes can be connected continuously to defibrillation port 310, etc. Either way, defibrillation port 310 can be used for guiding via electrodes to person 82 an electrical charge that has been stored in defibrillator 300, as will be seen later in this document.

If defibrillator 300 is actually a defibrillator-monitor, as was described with reference to FIG. 2, then it will typically also have an ECG port 319 in housing 301, for plugging in ECG leads 309. ECG leads 309 can help sense an ECG signal, e.g. a 12-lead signal, or from a different number of leads. Moreover, a defibrillator-monitor could have additional ports (not shown), and an other component 325 for the above described additional features, such as patient signals.

Defibrillator 300 also includes a measurement circuit 320. Measurement circuit 320 receives physiological signals from ECG port 319, and also from other ports, if provided. These physiological signals are sensed, and information about them is rendered by circuit 320 as data, or other signals, etc.

If defibrillator 300 is actually an AED, it may lack ECG port 319. Measurement circuit 320 can obtain physiological signals through nodes 314, 318 instead, when defibrillation electrodes 304, 308 are attached to person 82. In these cases, a person's ECG signal can be sensed as a voltage difference between electrodes 304, 308. Plus, impedance between electrodes 304, 308 can be sensed for detecting, among other things, whether these electrodes 304, 308 have been inadvertently disconnected from the person.

Defibrillator 300 also includes a processor 330. Processor 330 may be implemented in any number of ways. Such ways include, by way of example and not of limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 330 can be considered to have a number of modules. One such module can be a detection module 332, which senses outputs of measurement circuit 320. Detection module 332 can include a VF detector. Thus, the person's sensed ECG can be used to determine whether the person is experiencing VF.

Another such module in processor 330 can be an advice module 334, which arrives at advice based on outputs of detection module 332. Advice module 334 can include a Shock Advisory Algorithm, implement decision rules, and so on. The advice can be to shock, to not shock, to administer other forms of therapy, and so on. If the advice is to shock, some external defibrillator embodiments merely report that to the user, and prompt them to do it. Other embodiments further execute the advice, by administering the shock. If the advice is to administer CPR, defibrillator 300 may further issue prompts for it, and so on.

Processor 330 can include additional modules, such as module 336, for other functions. In addition, if other component 325 is indeed provided, it may be operated in part by processor 330, etc.

Defibrillator 300 optionally further includes a memory 338, which can work together with processor 330. Memory 338 may be implemented in any number of ways. Such ways include, by way of example and not of limitation, nonvolatile memories (NVM), read-only memories (ROM), random access memories (RAM), any combination of these, and so on. Memory 338, if provided, can include programs for processor 330, and so on. The programs can be operational for the inherent needs of processor 330, and can also include protocols and ways that decisions can be made by advice module 334. In addition, memory 338 can store prompts for user 380, etc. Moreover, memory 338 can store patient data.

Defibrillator 300 may also include a power source 340. To enable portability of defibrillator 300, power source 340 typically includes a battery. Such a battery is typically implemented as a battery pack, which can be rechargeable or not. Sometimes, a combination is used, of rechargeable and non-rechargeable battery packs. Other embodiments of power source 340 can include AC power override, for where AC power will be available, and so on. In some embodiments, power source 340 is controlled by processor 330.

Defibrillator 300 additionally includes an energy storage module 350. Module 350 is where some electrical energy is stored, when preparing it for sudden discharge to administer a shock. Module 350 can be charged from power source 340 to the right amount of energy, as controlled by processor 330. In typical implementations, module 350 includes one or more capacitors 352, and so on.

Defibrillator 300 moreover includes a discharge circuit 355. Circuit 355 can be controlled to permit the energy stored in module 350 to be discharged to nodes 314, 318, and thus also to defibrillation electrodes 304, 308. Circuit 355 can include one or more switches 357. Those can be made in a number of ways, such as by an H-bridge, and so on.

Defibrillator 300 further includes a user interface 370 for user 380. User interface 370 can be made in any number of ways. For example, interface 370 may include a screen, to display what is detected and measured, provide visual feedback to the rescuer for their resuscitation attempts, and so on. Interface 370 may also include a speaker, to issue voice prompts, etc. Interface 370 may additionally include various controls, such as pushbuttons, keyboards, and so on. In addition, discharge circuit 355 can be controlled by processor 330, or directly by user 380 via user interface 370, and so on.

Defibrillator 300 can optionally include other components. For example, a communication module 390 may be provided for communicating with other machines. Such communication can be performed wirelessly, or via wire, or by infrared communication, and so on. This way, data can be communicated, such as patient data, incident information, therapy attempted, CPR performance, and so on.

FIGS. 4A-4C illustrate interactions between a first external defibrillator 401 and a second external defibrillator 402, such as the external defibrillator 300 of FIG. 3, according to embodiments.

FIG. 4A is a diagram showing the two external defibrillators 401 and 402 before being bumped together according to embodiments. The two external defibrillators 401 and 402 may approach each other as indicated by arrows 403. For example, a user may move the first external defibrillator 401 toward the second external defibrillator 402. Alternatively or in addition thereto, the user or another user may move the second external defibrillator 402 toward the first external defibrillator 401.

FIG. 4B is a diagram showing the two external defibrillators 401 and 402 of FIG. 4A being bumped together, according to embodiments. For example, a user may move the first external defibrillator 401 toward the second external defibrillator 402 until a physical contact between the two devices occurs. Alternatively or in additional thereto, the user or another user may move the second external defibrillator 402 toward the first external defibrillator 401 until the two devices physically contact each other.

FIG. 4C is a diagram showing the two external defibrillators 401 and 402 of FIG. 4B establishing a communication link ("comlink") 404, after having been bumped together according to embodiments. The comlink 404 is bidirectional, as indicated in the diagram. In certain embodiments, the second external defibrillator 402 may subsequently transmit a data signal to the first external defibrillator 401, as indicated by 405. The comlink 404 may be wireless and, consequently, the data signal transmission 405 may also be wireless. The data signal may encode event data that the first external defibrillator 401 may decode subsequent to receiving the data signal from the second external defibrillator 402.

Figure 5:
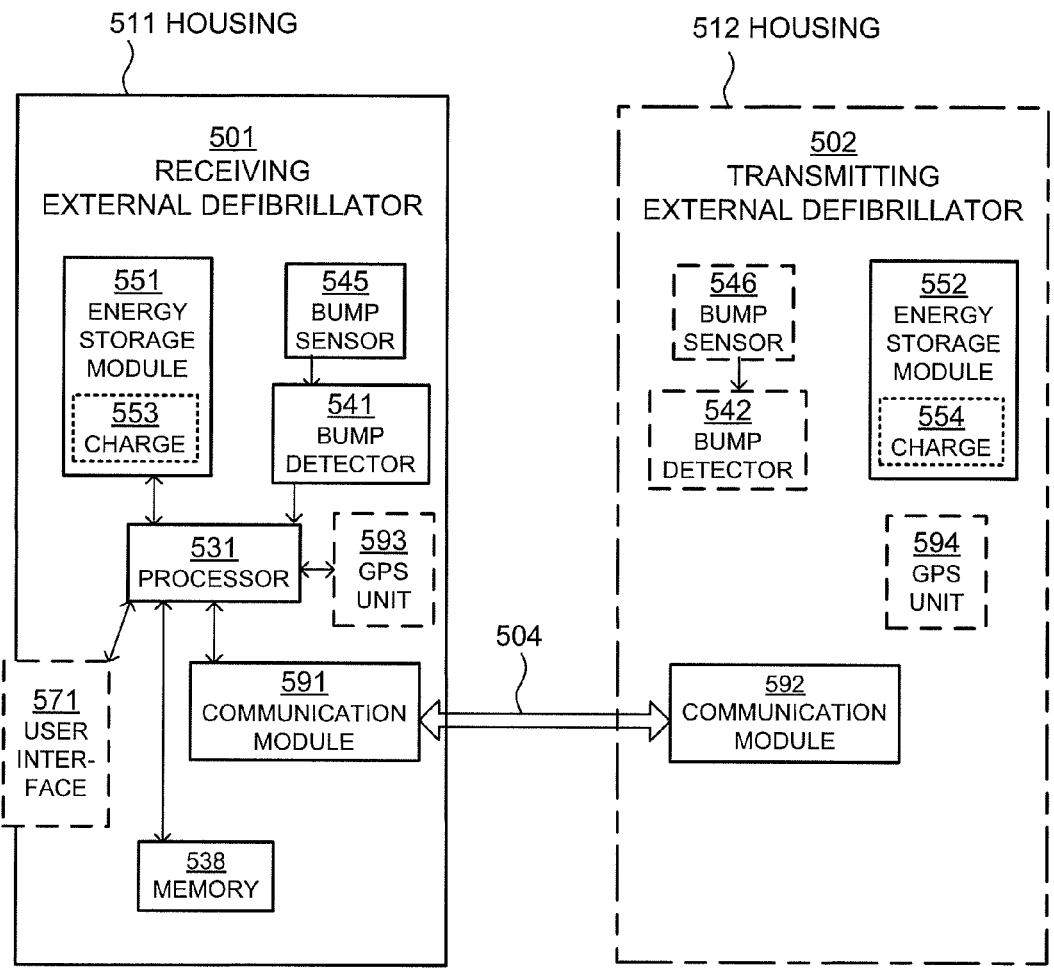
FIG. 5 is a block diagram showing components of an external defibrillator initiating reception of event data upon being bumped according to embodiments.

FIG. 5 is a block diagram showing components of a receiving external defibrillator 501, such as the first external defibrillator 401 of FIGS. 4A-4C, initiating reception of event data upon being bumped according to embodiments. In certain embodiments, the receiving external defibrillator 501 receives resuscitation event data from a transmitting external defibrillator 502 that is distinct from the receiving external defibrillator 501.

The receiving external defibrillator 501 includes a first housing 511, a first energy storage module 551 in an interior of the first housing 511 for storing a first electrical charge 553, a first defibrillation port (not shown) for guiding via electrodes the first electrical charge 553 to the person, and a first wireless communication module 591.

The transmitting external defibrillator 502 includes a second housing 512, a second energy storage module 552 in the second housing 512 for storing a second electrical charge 554, a second defibrillation port (not shown) for guiding via electrodes the second electrical charge 554 to a person, and a second wireless communication module 592.

The receiving external defibrillator 501 includes a bump sensor 545 in the interior of the first housing 511, for generating motion information of the first housing 511, and a bump detector 541 configured to determine whether the first housing 511 of the receiving external defibrillator 501 has been subjected to a local bump event based on the generated motion information. In certain embodiments, a local bump event is determined to have occurred if the motion information is interpreted as a deceleration event with a value larger than a preset threshold. The transmitting external defibrillator 502 may optionally include a bump sensor 546 in the interior of the second housing 512, and a bump detector 542.

The receiving external defibrillator 501 includes a processor 531 configured to, responsive to a determination that a local bump event has occurred, cause the first communication module 592 to establish a wireless communication link 504 with the second communication module 592, the first communication module 591 being further adapted to receive wirelessly a data signal transmitted by the second communication module 592 over the communication link 504, the data signal encoding event data stored in the transmitting external defibrillator 502 about when the second electrical charge 554 was guided to the person. In certain embodiments, the receiving external defibrillator 501 also includes a memory 538 adapted to store the resuscitation event data after being received and decoded from the data signal.

The receiving external defibrillator 501 may optionally include a user interface 571. In such embodiments, a confirmation request may be caused to be output via the user interface 571 responsive to the determination that the local bump event has occurred. Also, the communication link 504 may be caused to be established responsive to receiving by a user a user confirmation in response to the confirmation request.

In certain embodiments, establishing the communication link 504 includes causing the first communication module 591 to transmit a readiness signal, and the data signal is transmitted by the second communication module 592 responsive to receiving the readiness signal. The readiness signal may communicate identification information about the receiving external defibrillator 501, for example.

In certain embodiments, establishing the communication link 504 includes receiving an availability signal that is generated by the transmitting external defibrillator 502. The availability signal may communicate identification information about the transmitting external defibrillator 502, for example.

In certain embodiments, establishing the communication link 504 includes establishing a bump confirmation that the local bump event also involved the transmitting external defibrillator 502, and the data signal is received only if the local bump confirmation is established. In some of these embodiments, establishing the communication link 504 further includes causing the first communication module 591 to transmit a readiness signal. The readiness signal may be output with either a preset time delay after a time of the local bump event or a randomized time delay within a preset time after the local bump event. The readiness signal may encode a time indication associated with the occurrence of the local bump event.

In certain embodiments, establishing the communication link 504 further includes receiving an availability signal that is generated by the transmitting external defibrillator 502, a time of a remote bump event of the transmitting external defibrillator 502 is determined from the availability signal, and the bump confirmation is established by comparing the time of the remote bump event with a time of the local bump event. For the time comparison, the availability signal may be presumed output with a preset time delay after a time of the remote bump event. The availability signal may encode the time indication of the remote bump event.

The receiving external defibrillator 501 may optionally include a first global positioning system (GPS) unit 593. The first GPS unit 593 may be configured to determine first GPS coordinates corresponding to the receiving external defibrillator 501. In certain embodiments, the transmitting external defibrillator 502 has a second GPS unit 594 configured to determine second GPS coordinates corresponding to the transmitting external defibrillator 502. In such embodiments, the communication link 504 may not be established unless or until the two devices are within a certain distance of each other as determined by comparing the first GPS coordinates and the second GPS coordinates. The determination may take into account a margin of error depending on the type of each GPS unit 593 and 594.

Figure 8:
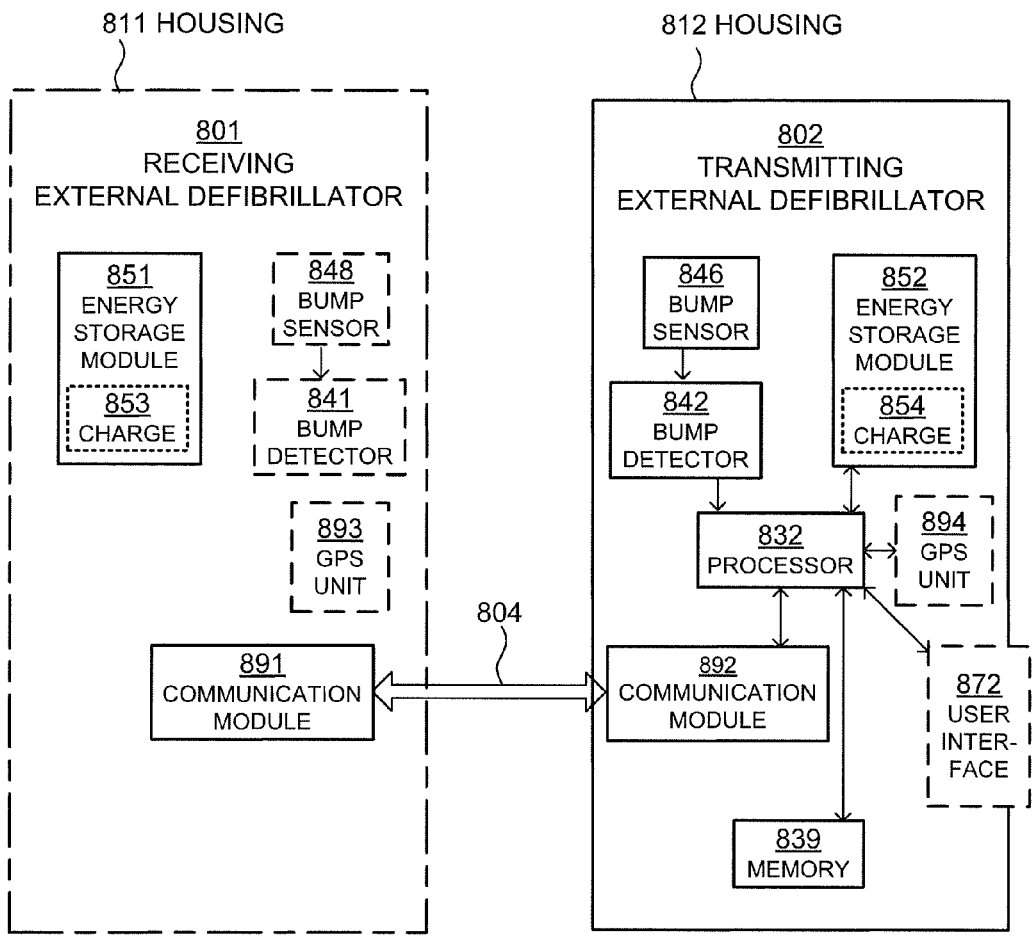
FIG. 8 is a block diagram showing components of an external defibrillator initiating transmission of event data upon being bumped according to embodiments.

FIG. 8 is a block diagram showing components of a transmitting external defibrillator 802, such as the second external defibrillator 402 of FIGS. 4A-4C, initiating transmission of event data upon being bumped according to embodiments. In certain embodiments, the transmitting external defibrillator 802 transmits resuscitation event data to a receiving external defibrillator 801 that is distinct from the transmitting external defibrillator 802.

The receiving external defibrillator 801 includes a first housing 811, a first energy storage module 851 in the first housing 811 for storing a first electrical charge 853, a first defibrillation port (not shown) for guiding via electrodes the first electrical charge 853 to a person, and a first wireless communication module 891. In certain embodiments, the receiving external defibrillator 801 also includes a first GPS unit 893 configured to determine first GPS coordinates corresponding to the receiving external defibrillator 801.

The transmitting external defibrillator 802 includes a second housing 812, a second energy storage module 852 in an interior of the second housing 812 for storing a second electrical charge 854, a second defibrillation port (not shown) for guiding via electrodes the second electrical charge 854 to the person, and a second wireless communication module 892.

The transmitting external defibrillator 802 also includes a bump sensor 846 in the interior of the second housing 812, for generating motion information of the second housing 812, and a bump detector 842 configured to determine whether the second housing 812 of the transmitting external defibrillator 802 has been subjected to a local bump event based on the generated motion information. In certain embodiments, a local bump event is determined to have occurred if the motion information is interpreted as a deceleration event with a value larger than a preset threshold. The receiving external defibrillator 801 may optionally include a bump sensor 848 in the interior of the first housing 811, and a bump detector 841.

The transmitting external defibrillator 802 includes a processor 832 configured to, responsive to a determination that a local bump event has occurred, cause the second communication module 892 to establish a wireless communication link 804 with the first communication module 891, the second communication module 892 being further adapted to transmit a data signal that encodes the resuscitation event data over the communication link 804. In certain embodiments, the transmitting external defibrillator 802 also includes a memory 839 adapted to store event data about when the second electrical charge 854 was guided to the person.

The transmitting external defibrillator 802 may optionally include a user interface 872. In such embodiments, a confirmation request may be caused to be output via the user interface 872 responsive to the determination that the local bump event has occurred. Also, the communication link 804 may be caused to be established responsive to receiving by a user a user confirmation in response to the confirmation request.

In certain embodiments, establishing the communication link 804 includes causing the second communication module 892 to transmit an availability signal, and the data signal is transmitted by the second communication module 892 responsive to the first communication module 891 receiving the availability signal. In certain embodiments, the availability signal communicates identification information about the transmitting external defibrillator 802.

In certain embodiments, establishing the communication link 804 includes receiving a readiness signal that is generated by the receiving external defibrillator 801. The readiness signal may communicate identification information about the receiving external defibrillator 801, for example.

In certain embodiments, establishing the communication link 804 includes establishing a bump confirmation that the local bump event also involved the receiving external defibrillator 801, and the data signal is transmitted only if the local bump confirmation is established. In some of these embodiments, establishing the communication link 804 further includes causing the second communication module 892 to transmit an availability signal. The availability signal may be output with either a preset time delay after a time of the local bump event or a randomized time delay within a preset time after the local bump event. The availability signal may encode a time indication associated with the occurrence of the local bump event.

In certain embodiments, establishing the communication link 804 further includes receiving a readiness signal that is generated by the receiving external defibrillator 801, a time of a remote bump event of the receiving external defibrillator 801 is determined from the readiness signal, and the bump confirmation is established by comparing the time of the remote bump event with a time of the local bump event. For the time comparison, the readiness signal may be presumed output with a preset time delay after a time of the remote bump event. The readiness signal may encode the time indication of the remote bump event.

The transmitting external defibrillator 802 may optionally include a second GPS unit 893. The second GPS unit 893 may be configured to determine second GPS coordinates corresponding to the transmitting external defibrillator 802. In certain embodiments, the transmitting external defibrillator 802 has a second GPS unit 894 configured to determine second GPS coordinates corresponding to the transmitting external defibrillator 802. In such embodiments, the communication link 804 may not be established unless or until the two devices are within a certain distance of each other as determined by comparing the first GPS coordinates and the second GPS coordinates. The determination may take into account a margin of error depending on the type of each GPS unit 893 and 894.

FIG. 11 is a block diagram showing systems for transferring event data that include an external defibrillator 1102 and a defibrillator-monitor 1101 according to embodiments. The external defibrillator 1102 is often an Automated External Defibrillator (AED). In certain embodiments, a user may cause a transfer of data such as resuscitation event data pertaining to a person, for example, between the external defibrillator 1102 and the defibrillator-monitor 1101 by bumping the external defibrillator 1102 into the defibrillator-monitor 1101.

In certain embodiments, a data signal encoding resuscitation event data, for example, may be transferred from the defibrillator-monitor 1101 directly to an other external device 1108, or to a remote device 1112, such as in a treatment center, by way of a communication network 1110 such as the Internet. The other external device 1108 may also communicate with the remote device 1112 or with other devices not shown by way of the network 1110.

The functions of this description may be implemented by one or more devices that include logic circuitry. The device performs functions and/or methods as are described in this document. The logic circuitry may include a processor that may be programmable for a general purpose, or dedicated, such as microcontroller, a microprocessor, a Digital Signal Processor (DSP), etc. For example, the device may be a digital computer like device, such as a general-purpose computer selectively activated or reconfigured by a computer program stored in the computer. Alternately, the device may be implemented by an Application Specific Integrated Circuit (ASIC), etc.

Moreover, methods are described below. The methods and algorithms presented herein are not necessarily inherently associated with any particular computer or other apparatus. Rather, various general-purpose machines may be used with programs in accordance with the teachings herein, or it may prove more convenient to construct more specialized apparatus to perform the required method steps. The required structure for a variety of these machines will become apparent from this description.

In all cases there should be borne in mind the distinction between methods in this description, and the method of operating a computing machine. This description relates both to methods in general, and also to steps for operating a computer and for processing electrical or other physical signals to generate other desired physical signals.

Programs are additionally included in this description, as are methods of operation of the programs. A program is generally defined as a group of steps leading to a desired result, due to their nature and their sequence. A program is usually advantageously implemented as a program for a computing machine, such as a general-purpose computer, a special purpose computer, a microprocessor, etc.

Storage media are additionally included in this description. Such media, individually or in combination with others, have stored thereon instructions of a program made according to the invention. A storage medium according to the invention is a computer-readable medium, such as a memory, and is read by the computing machine mentioned above.

Performing the steps or instructions of a program requires physical manipulations of physical quantities. Usually, though not necessarily, these quantities may be transferred, combined, compared, and otherwise manipulated or processed according to the instructions, and they may also be stored in a computer-readable medium. These quantities include, for example electrical, magnetic, and electromagnetic signals, and also states of matter that can be queried by such signals. It is convenient at times, principally for reasons of common usage, to refer to these quantities as bits, data bits, samples, values, symbols, characters, images, terms, numbers, or the like. It should be borne in mind, however, that all of these and similar terms are associated with the appropriate physical quantities, and that these terms are merely convenient labels applied to these physical quantities, individually or in groups.

This detailed description is presented largely in terms of flowcharts, display images, algorithms, and symbolic representations of operations of data bits within at least one computer readable medium, such as a memory. Indeed, such descriptions and representations are the type of convenient labels used by those skilled in programming and/or the data processing arts to effectively convey the substance of their work to others skilled in the art. A person skilled in the art of programming may use these descriptions to readily generate specific instructions for implementing a program according to the present invention.

Often, for the sake of convenience only, it is preferred to implement and describe a program as various interconnected distinct software modules or features, individually and collectively also known as software. This is not necessary, however, and there may be cases where modules are equivalently aggregated into a single program with unclear boundaries. In any event, the software modules or features of this description may be implemented by themselves, or in combination with others. Even though it is said that the program may be stored in a computer-readable medium, it should be clear to a person skilled in the art that it need not be a single memory, or even a single machine. Various portions, modules or features of it may reside in separate memories, or even separate machines. The separate machines may be connected directly, or through a network, such as a local access network (LAN), or a global network, such as the Internet.

It will be appreciated that some of these methods may include software steps that may be performed by different modules of an overall software architecture. For example, data forwarding in a router may be performed in a data plane, which consults a local routing table. Collection of performance data may also be performed in a data plane. The performance data may be processed in a control plane, which accordingly may update the local routing table, in addition to neighboring ones. A person skilled in the art will discern which step is best performed in which plane.

An economy is achieved in the present document in that a single set of flowcharts is used to describe both programs, and also methods. So, while flowcharts are described in terms of boxes, they can mean both method and programs.

For this description, the methods may be implemented by machine operations. In other words, embodiments of programs are made such that they perform methods of the invention that are described in this document. These may be optionally performed in conjunction with one or more human operators performing some, but not all of them. As per the above, the users need not be collocated with each other, but each only with a machine that houses a portion of the program. Alternately, some of these machines may operate automatically, without users and/or independently from each other.

Methods are now described.

Figure 6:
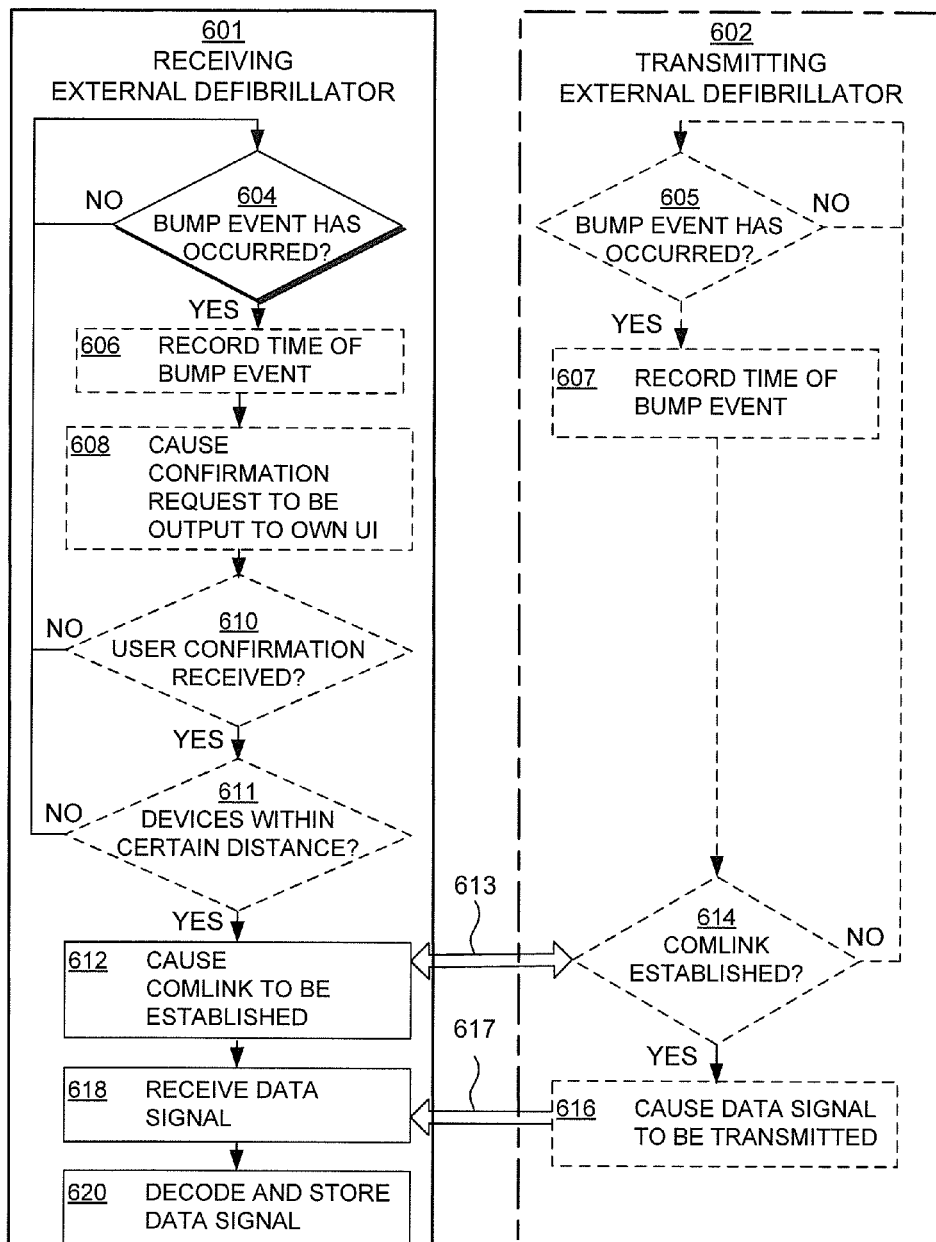
FIG. 6 is a flowchart for illustrating example methods executable by external defibrillators according to embodiments.

FIG. 6 is a flowchart for illustrating methods 600 executable by external defibrillators according to embodiments. In an operation at 604, a receiving external defibrillator 601, such as the receiving external defibrillator 501 of FIG. 5, determines whether a local bump event has occurred. Responsive to a determination that the local bump event has occurred, the method 600 proceeds beyond the operation at 604; otherwise, the operation at 604 repeats. Responsive to the determination that the local bump event has occurred, the receiving external defibrillator 601 may optionally record a time of the local bump event, as indicated by 606.

In certain embodiments, a transmitting external defibrillator 602, such as the transmitting external defibrillator 502 of FIG. 5, also determines whether the local bump event has occurred, as indicated by 605. Responsive to a determination that the local bump event has occurred, the method 600 proceeds beyond the operation at 605; otherwise, the operation at 605 repeats. Responsive to the transmitting external defibrillator 602 determining that the local bump event has occurred, the transmitting external defibrillator 602 may optionally record a time of the local bump event, as indicated by 607.

In an optional operation at 608, the receiving external defibrillator 601 causes a user confirmation request to be output to a user interface (UI) of the receiving external defibrillator 601. In a subsequent optional operation at 610, a determination is made as to whether a user confirmation is received from a user responsive to the user confirmation request being output to the user interface. Responsive to a determination that the user confirmation is received, the method 600 may proceed; otherwise, the method 600 returns to the operation at 604.

In an optional operation at 611, the receiving external defibrillator 601 determines whether the transmitting external defibrillator 602 is within a certain distance. For example, a first GPS unit of the receiving external defibrillator 601 may determine first GPS coordinates corresponding to the receiving external defibrillator 601 and compare them to second GPS coordinates corresponding to the transmitting external defibrillator 602. In certain embodiments, the second GPS coordinates corresponding to the transmitting external defibrillator 602 are determined by a second GPS unit of the transmitting external defibrillator 602.

Responsive to a determination that the transmitting external defibrillator 602 is not within the certain distance, e.g., the transmitting external defibrillator 602 is beyond a predetermined distance, based on the comparison between the first and second GPS coordinates, the method 600 may return to the operation at 604 and the receiving external defibrillator 601 may send a message or alert to the transmitting external defibrillator 602 or other device; otherwise, the method 600 may proceed to the operation at 612.

In an operation at 612, the receiving external defibrillator 601 communicates with a transmitting external defibrillator 602, as indicated by 613, to establish a communication link ("comlink") 617 with the transmitting external defibrillator 602 responsive to the determination that the local bump event has occurred.

At 614, the transmitting external defibrillator 602 may determine whether the communication link 617 has been established. If the communication link 617 has not been established, the method 600 returns to the operation at 605. In an operation at 616, the transmitting external defibrillator 602 may cause a data signal to be transmitted from the transmitting external defibrillator 602 over the communication link 617 responsive to a determination that the communication link 617 has been established.

In an operation at 618, the receiving external defibrillator 601 receives the data signal from the transmitting external defibrillator 602 over the communication link 617. In certain embodiments, the data signal encodes resuscitation event data stored in the transmitting external defibrillator 602, such as event data about when a stored electrical charge in the transmitting external defibrillator 602 was guided to a person.

In an operation at 620, the receiving external defibrillator 601 decodes resuscitation event data from the received data signal and stores the decoded resuscitation event data within the receiving external defibrillator 601. For example, the receiving external defibrillator 601 may store the decoded resuscitation event data in a memory of the receiving external defibrillator 601.

Figure 7:
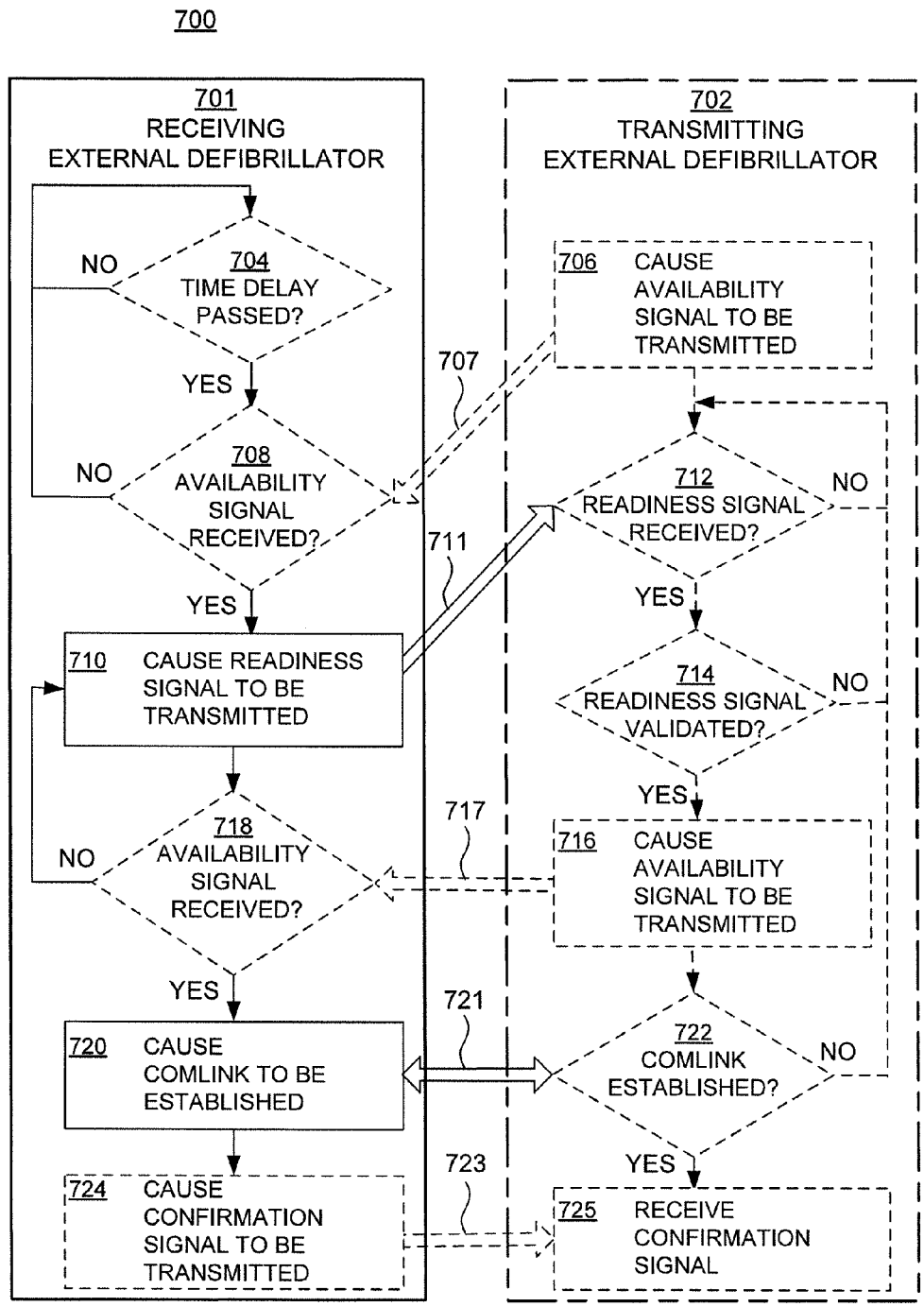
FIG. 7 is a flowchart for illustrating example methods executable by external defibrillators according to embodiments.

FIG. 7 is a flowchart for illustrating methods 700 executable by external defibrillators according to embodiments. The methods 700 illustrated in FIG. 7 generally pertain to the establishing of a communication link ("comlink") between a receiving external defibrillator 701, such as the receiving external defibrillator 601 of FIG. 6, and a transmitting external defibrillator 702, such as the transmitting external defibrillator 602 of FIG. 6.

In an optional operation at 704, the receiving external defibrillator 701 determines whether a predetermined time delay has passed. Responsive to a determination that the predetermined time delay has passed, the method 700 may proceed beyond the operation at 704; otherwise, the operation at 704 repeats. For example, if a certain amount of time has not passed, the receiving external defibrillator 701 may determine that the receiving external defibrillator 701 is not yet ready to receive data from the transmitting external defibrillator 702.

In an operation at 706, the transmitting external defibrillator 702 causes an availability signal to be transmitted to the receiving external defibrillator 701, as indicated by 707. In an optional operation at 708, the receiving external defibrillator 701 determines whether the availability signal has been received from the transmitting external defibrillator 702.

In an operation at 710, the receiving external defibrillator 701 causing a readiness signal to be transmitted to the transmitting external defibrillator 702, as indicated by 711. In an operation at 712, the transmitting external defibrillator 702 determines whether the readiness signal has been received from the receiving external defibrillator 701. In a subsequent operation at 714, the transmitting external defibrillator 702 determines whether the readiness signal is valid. In an operation at 716, the transmitting external defibrillator 702 causes an availability signal to be transmitted to the receiving external defibrillator 701, as indicated by 717, responsive to a determination that the readiness signal has been validated. In an optional operation at 718, the receiving external defibrillator 701 determines whether the availability signal has been received from the transmitting external defibrillator 702.

In an operation at 720, the receiving external defibrillator 701 causes a communication link ("comlink") to be established with the transmitting external defibrillator 702, as indicated by 721. In an operation at 722, the transmitting external defibrillator 702 determines whether the communication link has been established. Responsive to a determination that the communication link has been established, the method 700 proceeds beyond the operation at 722; otherwise, the method 700 returns to the operation at 712.

In an optional operation at 724, the receiving external defibrillator 701 causes a confirmation signal to be transmitted to the transmitting external defibrillator 702 responsive to the communication link being established, as indicated by 723. In a subsequent operation at 725, the transmitting external defibrillator 702 receives the confirmation signal from the receiving external defibrillator 701.

FIG. 9 is a flowchart for illustrating methods 900 executable by external defibrillators according to embodiments. In an operation at 904, a transmitting external defibrillator 902, such as the transmitting external defibrillator 802 of FIG. 8, stores resuscitation event data in a memory of the transmitting external defibrillator 902. The resuscitation event data may pertain to the delivery of a stored electric charge in the transmitting external defibrillator 902 to a person, for example.

In an operation at 906, the transmitting external defibrillator 902 determines whether a local bump event has occurred. Responsive to a determination that the local bump event has occurred, the method 900 proceeds beyond the operation at 906; otherwise, the operation at 906 repeats. Responsive to the determination that the local bump event has occurred, the transmitting external defibrillator 902 may optionally record a time of the local bump event, as indicated by 908.

In certain embodiments, a receiving external defibrillator 901, such as the receiving external defibrillator 801 of FIG. 8, also determines whether the local bump event has occurred, as indicated by 907. Responsive to a determination that the local bump event has occurred, the method 900 proceeds beyond the operation at 907; otherwise, the operation at 907 repeats. Responsive to the receiving external defibrillator 901 determining that the local bump event has occurred, the receiving external defibrillator 901 may optionally record a time of the local bump event, as indicated by 909.

In an operation at 914, the transmitting external defibrillator 902 causes a communication link 917 to be established with the receiving external defibrillator 901, as indicated by 915, responsive to determining that the local bump event has occurred. In an operation at 911, the receiving external defibrillator 901 determines whether the communication link has been established. Responsive to a determination that the communication link has been established, the method 900 proceeds beyond the operation at 911; otherwise, the method 900 returns to the operation at 907.

In a subsequent operation at 916, the transmitting external defibrillator 902 causes a data signal to be transmitted over the communication link 917 to the receiving external defibrillator 901, the data signal including the resuscitation event data. In an operation at 918, the receiving external defibrillator 901 receives the data signal from the transmitting external defibrillator 902.

In an optional operation at 910, the transmitting external defibrillator 902 causes a user confirmation request to be output to a user interface of the receiving external defibrillator 901. In an operation at 912, the transmitting external defibrillator 902 determines whether a user confirmation has been received. Responsive to receiving a user confirmation from a user responsive to the user confirmation request being output to the user interface, the method 900 may proceed; otherwise the method 900 returns to the operation at 906.

In another optional operation at 913, the transmitting external defibrillator 902 determines whether the receiving external defibrillator 901 is within a certain distance. For example, a GPS unit of the transmitting external defibrillator 902 may determine GPS coordinates corresponding to the transmitting external defibrillator 902 and compare them to GPS coordinates corresponding to the receiving external defibrillator 901. In certain embodiments, the GPS coordinates corresponding to the receiving external defibrillator 901 are determined by a GPS unit of the receiving external defibrillator 901.

Responsive to a determination that the receiving external defibrillator 901 is not within the certain distance, e.g., the receiving external defibrillator 901 is beyond a predetermined distance, based on the comparison between the GPS coordinates of the two devices, the method 900 returns to the operation at 906 and the transmitting external defibrillator 902 may send a message or alert to the receiving external defibrillator 901 or other device; otherwise, the method 900 may proceed to the operation at 914.

FIG. 10 is a flowchart for illustrating methods 1000 executable by external defibrillators according to embodiments. The methods 1000 illustrated in FIG. 10 generally pertain to the establishing of a communication link ("comlink") between a receiving external defibrillator 1001, such as the receiving external defibrillator 901 of FIG. 9, and a transmitting external defibrillator 1002, such as the transmitting external defibrillator 902 of FIG. 9.

In an optional operation at 1004, the transmitting external defibrillator 1002 determines whether a predetermined time delay has passed. Responsive to a determination that the time delay has passed, the method 1000 proceeds beyond the operation at 1004; otherwise, the operation at 1004 repeats.

In an operation at 1006, the receiving external defibrillator 1001 causes a readiness signal to be transmitted to the transmitting external defibrillator 1002, as indicated by 1007. In an operation at 1008, the transmitting external defibrillator 1002 determines whether the readiness signal has been received from the receiving external defibrillator 1001.

In an operation at 1010, the transmitting external defibrillator 1002 causes an availability signal to be transmitted to the receiving external defibrillator 1001, as indicated by 1011, responsive to a determination that the readiness signal has been received from the receiving external defibrillator 1001.

In an operation at 1012, the receiving external defibrillator 1001 determines whether the availability signal has been received from the transmitting external defibrillator 1002. In a subsequent operation at 1014, the receiving external defibrillator 1001 determines whether the availability signal is valid. In an operation at 1016, the receiving external defibrillator 1001 causes a readiness signal to be transmitted to the transmitting external defibrillator 1002, as indicated by 1017, responsive to a determination that the availability signal has been validated.

In an optional operation at 1018, the transmitting external defibrillator 1002 determines whether the readiness signal has been received from the receiving external defibrillator 1001. In a subsequent optional operation at 1020, the transmitting external defibrillator 1002 determines whether the readiness signal is valid.

In this description, numerous details have been set forth in order to provide a thorough understanding. In other instances, well-known features have not been described in detail in order to not obscure unnecessarily the description.

A person skilled in the art will be able to practice the present invention in view of this description, which is to be taken as a whole. The specific embodiments as disclosed and illustrated herein are not to be considered in a limiting sense. Indeed, it should be readily apparent to those skilled in the art that what is described herein may be modified in numerous ways. Such ways can include equivalents to what is described herein. In addition, the invention may be practiced in combination with other systems.

The following claims define certain combinations and sub-combinations of elements, features, steps, and/or functions, which are regarded as novel and non-obvious. Additional claims for other combinations and sub-combinations may be presented in this or a related document.

What is claimed is:

1. A transmitting external defibrillator for transmitting resuscitation event data to a receiving external defibrillator that is separate and distinct from the transmitting external defibrillator, the receiving external defibrillator including a first housing, a first energy storage module in the first housing for storing a first electrical charge, a first defibrillation port for guiding via electrodes the first electrical charge to a person, and a first wireless communication module, the transmitting external defibrillator comprising:
a second housing;
a second energy storage module in an interior of the second housing that stored a second electrical charge;
a second defibrillation port adapted to be coupled to electrodes, and via which the second electrical charge was guided to the person;
a memory in the interior of the second housing adapted to store event data about when the second electrical charge was guided to the person;
a bump sensor in the interior of the second housing, for generating motion information of the second housing;
a bump detector in the interior of the second housing configured to determine whether the second housing has been subjected to a local bump event based on the generated motion information, the local bump event including a physical touching of the transmitting and receiving external defibrillators;
a second wireless communication module in the interior of the second housing; and
a processor in the interior of the second housing configured to, responsive to a determination that a local bump event has occurred, cause the second communication module to establish a wireless communication link with the first communication module,
in which the second communication module is further adapted to transmit a data signal configured to encode the resuscitation event data over the communication link,
the bump detector is further configured to establish a bump confirmation that the local bump event also involved the receiving external defibrillator,
the second communication module is configured to only transmit the data signal responsive to the local bump confirmation being established,
the second communication module is further configured to transmit an availability signal, and
the availability signal is output with a preset time delay after a time of the local bump event.

2. The transmitting external defibrillator of claim 1, in which
the bump detector is configured to determine that a local bump event has occurred if the motion information is interpreted as representing a deceleration event having a value that is larger than a preset threshold.

3. The transmitting external defibrillator of claim 1, further comprising:
a user interface, and in which
the user interface is configured to cause a confirmation request to be output responsive to the determination that the local bump event has occurred, and
the second communication module is configured to cause the communication link to be established responsive to receiving from a user a user confirmation in response to the confirmation request.

4. The transmitting external defibrillator of claim 1, in which
the second communication module is configured to transmit an availability signal, and
the second communication module is further configured to transmit the data signal responsive to the first communication module receiving the availability signal transmitted by the second communication module.

5. The transmitting external defibrillator of claim 4, in which
the availability signal is adapted to communicate identification information about the transmitting external defibrillator.

6. The transmitting external defibrillator of claim 1, in which
establishing the communication link includes the transmitting external defibrillator receiving a readiness signal that is generated by the receiving external defibrillator.

7. The transmitting external defibrillator of claim 6, in which
the readiness signal is adapted to communicate identification information about the receiving external defibrillator.

8. The transmitting external defibrillator of claim 1, in which
the availability signal encodes a time indication associated with the occurrence of the local bump event.

9. The transmitting external defibrillator of claim 1, in which
establishing the communication link further includes the transmitting external defibrillator receiving a readiness signal that is generated by the receiving external defibrillator,
a time of a remote bump event of the receiving external defibrillator is determined from the readiness signal, and
the bump confirmation is established by comparing the time of the remote bump event with a time of the local bump event.

10. The transmitting external defibrillator of claim 9, in which
for the time comparison, the readiness signal encodes the time indication of the remote bump event.

11. The transmitting external defibrillator of claim 1, further comprising:
a global positioning system (GPS) unit configured to determine GPS coordinates corresponding to the transmitting external defibrillator, and in which
the processor is further configured to cause the second communication module to not establish a wireless communication link with the first communication module based on the GPS coordinates.

12. A transmitting external defibrillator for transmitting resuscitation event data to a receiving external defibrillator that is separate and distinct from the transmitting external defibrillator, the receiving external defibrillator including a first housing, a first energy storage module in the first housing for storing a first electrical charge, a first defibrillation port for guiding via electrodes the first electrical charge to a person, and a first wireless communication module, the transmitting external defibrillator comprising:
a second housing;
a second energy storage module in an interior of the second housing that stored a second electrical charge;
a second defibrillation port adapted to be coupled to electrodes, and via which the second electrical charge was guided to the person;

19 a memory in the interior of the second housing adapted to store event data about when the second electrical charge was guided to the person;

a bump sensor in the interior of the second housing, for generating motion information of the second housing;

a bump detector in the interior of the second housing configured to determine whether the second housing has been subjected to a local bump event based on the generated motion information, the local bump event including a physical touching of the transmitting and receiving external defibrillators;

a second wireless communication module in the interior of the second housing; and a processor in the interior of the second housing configured to, responsive to a determination that a local bump event has occurred, cause the second communication module to establish a wireless communication link with the first communication module, in which the second communication module is further adapted to transmit a data signal configured to encode the resuscitation event data over the communication link, the bump detector is further configured to establish a bump confirmation that the local bump event also involved the receiving external defibrillator, the second communication module is configured to only transmit the data signal responsive to the local bump confirmation being established, the second communication module is further configured to transmit an availability signal, and the availability signal is output with a randomized time delay within a preset time after the local bump event.

13. The transmitting external defibrillator of claim 12, in which the bump detector is configured to determine that a local bump event has occurred if the motion information is interpreted as representing a deceleration event having a value that is larger than a preset threshold.

14. The transmitting external defibrillator of claim 12, further comprising:

a user interface, and in which the user interface is configured to cause a confirmation request to be output responsive to the determination that the local bump event has occurred, and the second communication module is configured to cause the communication link to be established responsive to receiving from a user a user confirmation in response to the confirmation request.

15. The transmitting external defibrillator of claim 12, in which the second communication module is configured to transmit an availability signal, and the second communication module is further configured to transmit the data signal responsive to the first communication module receiving the availability signal transmitted by the second communication module.

16. The transmitting external defibrillator of claim 15, in which the availability signal is adapted to communicate identification information about the transmitting external defibrillator.

17. The transmitting external defibrillator of claim 12, in which establishing the communication link includes the transmitting external defibrillator receiving a readiness signal that is generated by the receiving external defibrillator.

20

18. The transmitting external defibrillator of claim 17, in which the readiness signal is adapted to communicate identification information about the receiving external defibrillator.

19. The transmitting external defibrillator of claim 12, in which the availability signal encodes a time indication associated with the occurrence of the local bump event.

20. The transmitting external defibrillator of claim 12, in which establishing the communication link further includes the transmitting external defibrillator receiving a readiness signal that is generated by the receiving external defibrillator, a time of a remote bump event of the receiving external defibrillator is determined from the readiness signal, and the bump confirmation is established by comparing the time of the remote bump event with a time of the local bump event.

21. The transmitting external defibrillator of claim 20, in which for the time comparison, the readiness signal encodes the time indication of the remote bump event.

22. The transmitting external defibrillator of claim 12, further comprising:

a global positioning system (GPS) unit configured to determine GPS coordinates corresponding to the transmitting external defibrillator, and in which the processor is further configured to cause the second communication module to not establish a wireless communication link with the first communication module based on the GPS coordinates.

23. A transmitting external defibrillator for transmitting resuscitation event data to a receiving external defibrillator that is separate and distinct from the transmitting external defibrillator, the receiving external defibrillator including a first housing, a first energy storage module in the first housing for storing a first electrical charge, a first defibrillation port for guiding via electrodes the first electrical charge to a person, and a first wireless communication module, the transmitting external defibrillator comprising:

a second housing;

a second energy storage module in an interior of the second housing that stored a second electrical charge;

a second defibrillation port adapted to be coupled to electrodes, and via which the second electrical charge was guided to the person;

a memory in the interior of the second housing adapted to store event data about when the second electrical charge was guided to the person;

a bump sensor in the interior of the second housing, for generating motion information of the second housing;

a bump detector in the interior of the second housing configured to determine whether the second housing has been subjected to a local bump event based on the generated motion information, the local bump event including a physical touching of the transmitting and receiving external defibrillators;

a second wireless communication module in the interior of the second housing; and a processor in the interior of the second housing configured to, responsive to a determination that a local bump event has occurred, cause the second communication module to establish a wireless communication link with the first communication module, in which the second communication module is further adapted to transmit a data signal configured to encode the resuscitation event data over the communication link, the bump detector is further configured to establish a bump confirmation that the local bump event also involved the receiving external defibrillator, the second communication module is configured to only transmit the data signal responsive to the local bump confirmation being established, and for the time comparison, the readiness signal is presumed output with a preset time delay after a time of the remote bump event.

24. The transmitting external defibrillator of claim 23, in which the bump detector is configured to determine that a local bump event has occurred if the motion information is interpreted as representing a deceleration event having a value that is larger than a preset threshold.

25. The transmitting external defibrillator of claim 23, further comprising:

a user interface, and in which the user interface is configured to cause a confirmation request to be output responsive to the determination that the local bump event has occurred, and the second communication module is configured to cause the communication link to be established responsive to receiving from a user a user confirmation in response to the confirmation request.

26. The transmitting external defibrillator of claim 23, in which the second communication module is configured to transmit an availability signal, and the second communication module is further configured to transmit the data signal responsive to the first communication module receiving the availability signal transmitted by the second communication module.

27. The transmitting external defibrillator of claim 26, in which the availability signal is adapted to communicate identification information about the transmitting external defibrillator.

28. The transmitting external defibrillator of claim 23, in which establishing the communication link includes the transmitting external defibrillator receiving a readiness signal that is generated by the receiving external defibrillator.

29. The transmitting external defibrillator of claim 28, in which the readiness signal is adapted to communicate identification information about the receiving external defibrillator.

30. The transmitting external defibrillator of claim 23, in which the availability signal encodes a time indication associated with the occurrence of the local bump event.

31. The transmitting external defibrillator of claim 23, in which establishing the communication link further includes the transmitting external defibrillator receiving a readiness signal that is generated by the receiving external defibrillator, a time of a remote bump event of the receiving external defibrillator is determined from the readiness signal, and the bump confirmation is established by comparing the time of the remote bump event with a time of the local bump event.

32. The transmitting external defibrillator of claim 30, in which for the time comparison, the readiness signal encodes the time indication of the remote bump event.

33. The transmitting external defibrillator of claim 23, further comprising:

a global positioning system (GPS) unit configured to determine GPS coordinates corresponding to the transmitting external defibrillator, and in which the processor is further configured to cause the second communication module to not establish a wireless communication link with the first communication module based on the GPS coordinates.

* * * * *